(12) United States Patent
Terstegge et al.

(10) Patent No.: US 7,790,456 B2
(45) Date of Patent: Sep. 7, 2010

(54) SCALABLE PROCESS FOR CULTIVATING UNDIFFERENTIATED STEM CELLS IN SUSPENSION

(75) Inventors: Stefanie Terstegge, Bonn (DE); Oliver Brüstle, Bonn (DE)

(73) Assignee: Rheinische Friedrich-Wilhelms-Universitat, Bonn (DE)

( * ) Notice: Subject to any disclaimer, the term of this patent is extended or adjusted under 35 U.S.C. 154(b) by 0 days.

(21) Appl. No.: 11/574,804

(22) PCT Filed: Sep. 9, 2005

(86) PCT No.: PCT/EP2005/009611

§ 371 (c)(1),
(2), (4) Date: Jul. 20, 2007

(87) PCT Pub. No.: WO2006/027229

PCT Pub. Date: Mar. 16, 2006

(65) Prior Publication Data

US 2007/0264713 A1    Nov. 15, 2007

(30) Foreign Application Priority Data

Sep. 7, 2004 (DE) ................. 10 2004 043 256

(51) Int. Cl.
*C12M 1/00* (2006.01)
*C12N 5/00* (2006.01)
*C12N 5/02* (2006.01)
*A01N 63/00* (2006.01)

(52) U.S. Cl. .................. 435/383; 435/289.1; 435/325; 435/384; 435/395; 435/403; 424/93.21

(58) Field of Classification Search .............. 424/93.21; 435/289.1, 325, 383, 384, 395, 403
See application file for complete search history.

(56) References Cited

U.S. PATENT DOCUMENTS

2003/0017589 A1    1/2003    Mandalam et al.

FOREIGN PATENT DOCUMENTS

WO    WO2004031369 A1 *    4/2004

OTHER PUBLICATIONS

Kim, B-S, 1998, Biotechnology Letters, vol. 20, No. 6, p. 595-601.*
Dang et al., "Controlled, Scalable Embryonic Stem Cell Differentiation Culture," *Stem Cells Rapid Communication* 22 (3): 275-282 (2004).
Gerecht-Nir et al., "Bioreactor Cultivation Enhances the Efficiency of Human Embryoid Body (hEB) Formation and Differentiation," *Biotechnology and Bioengineering*, 86 (5): 493-502 (2004).
Newman et al., "Poly (D,L lactic-co-glycolic acid) Microspheres as Biodegradable Microcarrier for Pluripotent Stem Cells," *Biomaterials*, 25 (26): 5763-5771 (2004).
International Search Report PCT/EP2005/009611 (2006).

* cited by examiner

*Primary Examiner*—Shin-Lin Chen
(74) *Attorney, Agent, or Firm*—Barnes & Thornburg LLP; Alice O. Martin (57) ABSTRACT

The invention relates to a process for cultivating undifferentiated stem cells in suspension and in particular to a method for cultivating stem cells on microcarriers in vessels. The method enables stem cells to be cultivated in a scalable process for the first time, without losing their pluripotentiality. Different types of vessels are suitable for cultivation, such as e.g. spinners and bioreactors. The option of precisely setting the cultivation conditions in said vessels aids the process of obtaining a pluripotentiality of the stem cells. the inventive method also permits large yields of stem cells of an unvarying quality to be produced.

34 Claims, 5 Drawing Sheets

SCALABLE PROCESS FOR CULTIVATING UNDIFFERENTIATED STEM CELLS IN SUSPENSION

CROSS-REFERENCE TO RELATED PATENT APPLICATIONS

This is a U.S. National phase application of international patent application no. PCT/EP2005/009611, filed Sep. 7, 2005, which claims priority to German patent application no. 10-2004-043256.2, filed Sep. 7, 2004, the contents of which are expressly incorporated herein by reference in their entirety.

BACKGROUND OF THE INVENTION

The generation of replacement tissue in cell culture, commonly known as "tissue engineering", the provision of surrogate cells for cell-based transplantation therapies, and the identification of new drugs using cell based high-throughput methods all represent important examples of innovative biotechnology-based applications. Stem cells in particular represent an important source for implementing such biotechnological applications because stem cells, in contrast to primary cells, can readily serve as a potentially unlimited source for obtaining differentiated, specific cell types. However, culturing stem cells, especially human embryonic stem cells, using controlled experimental conditions is not practicable according to the state of the art. Known culturing conditions are typically characterized by a lack of scalability of the cultivating process, the dependency on a co-culture system, and an inability to suitably control the experimental parameters. Until now, a scalable suspension culture of embryonic stem cells was demonstrated only for already differentiated cells known as "embryoid bodies". Specifically, a suspension culture of embryonic stem cells in the form of embryoid bodies was established using rotating-wall bioreactors (Gerecht Nir et al., Biotechnol Bioeng. 2004, 86(5): 493-502) and known agitation systems (Zandstra et al., Tissue Eng. 2003, 9: 767-778; Dang et al., Stem Cells 2004, 22(3):2 75-82; and Wartenberg et al. Lab Invest. 1998 October; 78(10): 1301-14). Techniques utilizing a rotating-wall bioreactor are suitable for producing an organo-type-like culture via the differentiation of stem cells in order to form tissue-like aggregates; however, such techniques exhibit the disadvantage of lacking scalability to produce a larger volume of cells. Moreover, all of these known cultivation methods are characterized by significant limitations when attempting to produce differentiating and differentiated stem cells. The cultivation of undifferentiated, pluripotent cells using these known culture strategies has simply not yet been realized. Generally, the cultivation of undifferentiated primate stem cells has proven to be very complex and furthermore, particularly sensitive to external influences.

SUMMARY OF THE INVENTION

An object of the present invention is to provide a method for cultivating undifferentiated stem cells. A further object of the invention is to allow a scalable and controllable process for cultivating these cells.

The solution to the above-described objectives is derived collectively from the claims, the following description and the figures. The present invention relates to a method for proliferating stem cells comprising introducing medium, microcarriers and stem cells into a container, cultivating the stem cells in said container, wherein the cells maintain their stem cell characteristics after initiating the culture, and retrieving cells from the container.

Various types of containers, including spinner bottles, regulated or unregulated bioreactors are suitable for the method. The medium in these containers can be agitated, wherein the agitation of the medium can be achieved using an agitator. Known and defined media can be used as the medium. In addition, the medium can be conditioned by preincubation with cells other than stem cells, including murine or human fibroblasts. The microcarriers to be used in method of the present invention can consist of a homogenous material or of a carrier material and a coating. Culture containers having various sizes, e.g., containers comprising at least 10 to 100 liters, can be used in the method of the invention. Microcarriers and medium can be removed continuously, wherein the removed microcarriers and medium can be replaced with fresh microcarriers and fresh medium. A preferred embodiment of the method of the invention is characterized in that the introduced stem cells maintain their stem cell characteristics after the cultivation has been initiated. A further embodiment is characterized in that the number of stem cells increases during cultivation when compared to the initial numbers of cells present in the culture.

DEFINITIONS

Oxygen Partial Pressure:

Oxygen partial pressure according to the invention is the oxygen composition of an air mixture, at which the cultivation of cells is occurring. When introducing gas into a culture container under an atmospheric oxygen partial pressure of 21% at 37° C., a dissolved oxygen concentration of 100% was reached in the aqueous medium.

Stem Cells:

In contrast to primary cells, stem cells can serve as a potentially unlimited source for the isolation of differentiated specific cell types (Poulsom R. et al., J. Pathol. 2002 July; 197 (4):441-56; Gepstein L. Circ Res. 2002 Nov. 15; 91(10):866-76). Stem cells in the context of this invention refer to cells having the ability to both regenerate, i.e. being able to proliferate while still maintaining their stem cell characteristics, and to develop via a process known as "differentiation" to one or more specialized cell types, for example, cardiac muscle cells, endothelial cells, cartilage cells, bone cells, fat cells, neuronal cells, hepatocytes or insulin producing cells (Wobus A M. Mol Aspects Med. 2001 June; 22(3): 149-64).

Other examples of stem cells include, but are not limited to, stem cells derived from blood present in an umbilical cord (Sanchez-Ramos J R., J Neurosci Res. 2002 Sep. 15; 69(6): 880-93.), neuronal stem cells (Hitoshi S. et al., Genes Dev. 2002 Apr. 1; 16(7):846-58. Okano H. J Neurosci Res. 2002 Sep. 15; 69(6):698-707), mesenchymal stem cells originating from the bone marrow or the peripheral blood (Jiang Y. et al., Exp Hematol. 2002 August; 30(8):896-904; Schwartz et al., J Clin Invest. 2002 May; 109(10):1291-302) in addition to stem cells derived from the skin (Toma et al., Nat Cell Biol. 2001 September; 3(9): 778-84), the pancreas (Means A L., Pancreatology. 2001; 1(6): 587-96), the liver (Suzuki A., et al., Cell Transplant. 2001; 10(4-5):393-6), the gut (Brittan M., J. Pathol. 2002 July; 197(4):492-509) or from fat tissue (Cannon B. et al., Methods Mol Biol. 2001; 155:213-24). Other important sources of stem cells include embryonic germ cells (Schamblott M I., et al., Proc Natl Acad Sci USA. 2001 Jan. 2; 98(1): 113-8), embryonic carcinoma cells (Friedrich, T. D. et al., Differentiation. 1983; 24, 60-64; Andrews, P. W., Biochim. Biophys. Acta. 1988; 948, 17-36), and "embryonic stem cells" (herein "ES" cells or "ESC"), which can be isolated from the inner cell mass of a blastocyst.

Embryonic stem cell lines have been established from a variety of species, including mouse (Evans M J, Kaufman M H., Nature. 1981 Jul. 9; 292(5819):154-6) and human (Thomson J A, et al., Science. 1998 Nov. 6; 282(5391): 1145-7). ESC are typically pluripotent stem cells, meaning they can differentiate into a variety of specific cell types (Wobus A M., Mol Aspects Med. 2001 June; 22(3): 149-64; Amit M, Itskovitz-Eldor J., J Anat. 2002 March; 200(Pt 3):225-32). Both human and murine ES have been effectively shown to differentiate into a variety of cell-types, including cardiac muscle cells (Klug et al. J. Clin. Invest. 1996 July; 98 (1):216-24; Mummary C. et al., J Anat. 2002 March; 200(Pt 3):233-42.; Xu C. et al., Circ Res. 2002 Sep. 20; 91(6):501-8), insulin-producing cells (Assady et al., Diabetes. 2001 August; 50(8): 1691-7; Soria B. Differentiation. 2001 October; 68(4-5):205-19.; Lumelsky M. et al., Science, 2001 May 18; 292(5520): 1389-94), neural precursor cells and neural cells (Schuldiner M. et al., Brain Res. 2001 Sep. 21; 913(2):201-5); Brüstle, O. et al, Science. 1999 Jul. 30; 285(5428):754-6); Okabe S, et al, Mech Dev. 1996 September; 59(1):89-102; Zhang S C et al, Nat. Biotechnol. 2001 December; 19(12):1129-33), endothelial cells (Levenberg S. Proc Natl Acad Sci USA. 2002 Apr. 2; 99(7):4391-6) and hematopoietic cells (Kaufmann D S., Proc Natl Acad Sci USA. 2001 Sep. 11; 98(19): 10716-21). Stem cell lines refer to ES-cells that are propagated in cell culture.

Somatic Cells:

The term "somatic cells" refers to cells that are able to undergo maturation or have already matured to one or more tissue-specific cell types. Somatic cells have the capacity to develop into numerous types of tissues, for example, bone, dental bone, cartilage, tendons, bone morrow stroma, neural tissue, skin, pancreas, liver, fat tissue, and muscle.

Feeder Cells:

Feeder cells refer to cells of a first type that are required for cultivating cells of a second type. In the context of cultivating ES-cells, feeder cells have the function of securing the survival, proliferation, and maintenance of ES-cell pluripotency. ES-cell pluripotency can be achieved by directly co-cultivating the cells of the first with cells having the second type or, alternatively, by cultivating the cells of the first type in a medium for a certain period of time and then subsequently providing these cells to cells of the second type. Prior to transferring the medium comprising cells of the first type to the cells of the second type, all cells of the first type are preferably removed from the medium. The feeder cells can be irradiated prior to the beginning of cultivation, or undergo treatment with Mitomycin C in order to prevent any further growth of these cells. In a preferred embodiment, the feeder cells are irradiated with gamma irradiation.

Containers:

Containers suitable for the method of the present invention include bioreactors, spinners, and other containers suitable for cultivating cells. The term "bioreactor" refers to a container suitable for the cultivation of eukaryotic cells, preferably animal cells, and more preferably for the cultivation of mammalian cells. The term "regulated bioreactor" refers to bioreactor systems, wherein at least the oxygen partial pressure in the culture medium can be measured and regulated using known devices. Suitable devices for measuring the oxygen partial pressure are, for instance, oxygen electrodes. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)). A typical cultivation volume of a regulated bioreactor is between 20 ml and 500 ml. Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 $cm^2$. The cells are cultivated along the entire inner surface of these flasks; the cells are coated with culture medium accomplished by a "rolling" motion, i.e. rotating the bottles about their own individual axis.

Microcarriers:

Microcarriers (or "carriers") of the present invention include support materials for cultivating adherent growing cells, in particular, animal cells in suspension. Microcarriers are also defined in the IUPAC Compendium of Chemical Terminology (2nd Edition, 1992, Vol. 64, p. 160). As mentioned above, microcarriers of the invention are, in particular, support materials, preferably spherical in form, for cultivating stem cells in suspension. Microcarriers consist preferably of a material selected form the group consisting of plastic, glass, ceramic, silicone, gelatin, dextran, cellulose and others. In addition, microcarriers can be pretreated in various ways including plasma treatment of the plastic surfaces that results in creating a hydrophilic surface, or the carriers can be coated (e.g. with gelatin, fibronectin, laminin, polyomithine, matrigel, or with binding motifs of the RGD binding domain of fibronectin). Other suitable commercially available microcarriers include Cytodex 1, Cytodex 3, Cytopore (Amersham Biosciences), Cultispher G, Cultispher S (Perbio), Pronectin, FACT (Sigma), Biosilon, Microhex 2D (Nunc), and Immoba-Sil (Dunn).

Media:

Media includes fluids containing ingredients that allow the cultivation of cells and/or promote proliferation of the cells. A medium can contain any of the following ingredients in a characteristic amount and concentration: isotonic salt solutions, buffers (e.g., bicarbonate/$CO_2$), amino acids, one or more carbon sources (e.g., glucose), antibiotics, serum, or substances replacing the serum, growth factors, hormones (e.g., insulin), vitamins, trace elements, albumin, transferrin, lipids, and phenol red as a pH indicator. In other embodiments, a commercially available medium such as Dulbecco's Modified Eagle's Medium (DMEM) is used. In other preferred embodiments, DMEM or other media are utilized, which are particularly suitable for the cultivation of stem cells, including Knockout DMEM and other media. Knockout DMEM is a medium optimized for cultivating undifferentiated stem cells (described by Goldsborough, M., et al. (1998), Focus, 20, 8).

Conditioned Medium:

Conditioned Medium for cultivating ES cells may comprise various components, including Knockout Medium with 20% serum replacement, 1% non essential amino acids, 0.5% L-glutamine and 0.1 mM β-mercaptoethanol, which have been conditioned by a suitable cell type for 24 hours. Prior to use, the medium is filtered and 4 ng/ml fibroblast growth factor (bFGF) is added. Cells suitable for such conditioning include primary murine fibroblasts, human fibroblasts, and fibroblast cell lines. These cells can either be capable of reproducing or mitotically inactivated by gamma irradiation or another like treatment. Between 100,000 and 200,000, preferably 140,000 cells per ml are typically used for the conditioning. The conditioning can occur in any known cell culture container, including a carrier-based bioreactor process.

The medium used for the conditioning may also contain serum, likewise, a defined medium such as Ex-Vivo (Cambrex) may also be utilized.

Stem Cell Medium:

The stem cell medium may be a conditioned medium consisting of Knockout DMEM with 20% serum replacement (Goldsborough, M., et al. (1998), Focus, 20, 8), 1% non essential amino acids, 0.5% L-glutamine and 0.1 mM β-mercaptoethanol, which has been conditioned by a suitable cell type for 24 hours. Prior to use, the medium is filtered and 4 ng/ml fibroblast growth factor (bFGF) is added. In another embodiment, a medium containing 20% fetal calf serum (FCS, fetal calf serum) instead of 20% serum replacement, and otherwise identical to above-described medium, is used.

An alternative stem cell medium includes Knockout DMEM with 15% serum replacement, 1% non essential amino acids, 2 mM L-glutamine and 0.1 mM β-mercaptoethanol, 4 ng/ml basic fibroblast growth factor (bFGF), 0.12 ng/ml tumor growth factor β1 (TGFβ1) and 1000 U/ml leukemia inhibitory factor protein (LIF) or ExVivo (Cambrex) with 40 ng/ml bFGF and 15 ng/ml flt3-Ligand (FMS-like tyrosine kinase 3-ligand).

Detection of Markers for Pluripotency:

Human undifferentiated embryonic stem cells express various stem cell markers, including SSEA-3, SSEA-4, Tra-1-60, Tra-1-81, Oct4, hTERT, Nanog, Cripto, Rex (described by Brivanlou A H et al., Science. 2003 May 9; 300(5621): 913-6; Henderson J K et al., Stem Cells. 2002; 20(4):329-37 and Ben-Shushan, E. et al. 1998; Mol. Cell. Biol. 18, 1866-1878). All of these markers are suitable for confirming any stem cell characteristics of the cultured cells. The expressed markers may be detected using any known detection method including immunofluorescence, FACS analysis, in situ hybridization, reverse transcriptase real time PCR, or northern blot or western blot techniques.

For example, cells can be washed in PBS, fixed in 4% paraformaldehyde (PFA) for 10 minutes, followed by a repeat wash in PBS, and permeabilized in 0.5% Triton for an additional 10 minutes for detecting the presence of Oct4 expression. Nonspecific binding of the antibodies is prevented by blocking such binding incubating the cells with 5% normal goat serum (NGS) and 0.1% triton for 60 minutes. Incubation of the cells with the first antibody (anti-Oct4-rabbit-IgG, Santa Cruz Biotechnology Inc., diluted 1:400 in 5% NGS+ 0.1% Triton) is performed at room temperature overnight. Subsequent washing of the cells with PBS and a further incubation with the second antibody (anti-rabbit-IgG-Cy3, Jackson Immuno Research, diluted 1:200 in 5% NGS+0.1% Triton) at room temperature for 60 minutes is then performed. After an additional rinse in PBS, the cells are then incubated with DAPI (Sigma) at a 1:10,000 dilution for 2 minutes followed by a further washing step in PBS.

Antibodies:

The term "antibody" refers to polyclonal and monoclonal antibodies. In addition, fragments and derivatives of these antibodies may also be used in the present invention.

General Techniques and Chemicals:

Generally known and practiced methods in the fields of molecular biology, cell biology, protein chemistry and antibody techniques are fully described in the continuously updated publications "Molecular Cloning: A Laboratory Manual", (Sambrook et al., Cold Spring Harbor); Current Protocols in Molecular Biology (F. M. Ausubel et al. Eds., Wiley & Sons); Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al., Eds., Wiley & Sons). Known techniques relating to cell culture and media are described in "Large Scale Mammalian Cell Culture (Hu et al., Curt. Opin., Biotechnol. 8: 148, 1997); "Serum free Media" (K. Kitano, Biotechnol. 17: 73, 1991); and "Suspension Culture of Mammalian Cells" (Birch et al. Bioprocess Technol. 19: 251, 1990). Methods directed to stem cells are described in "Teratocarcinoma and embryonic stem cells: A practical approach" (E. J. Robertson, ed., Press Ltd, 1987); "Guide to Techniques in Mouse Development" (P. M. Wassermann et al. eds., Academic Press, 1993); "Embryonic Stem Cell Differentiation in Vitro" (M. V. Wiles, Meth. Enzymol. 225: 900, 1993); "Properties and uses of Embryonic Stem Cells: Prospects for Application to Human Biology and Gene Therapy" (P. D. Rathjen et al., 1993); "Embryonic Stem Cells, Methods and Protocols" (K. Turksen ed., Humana Press, 2002) and "Human Embryonic Stem Cells" (A. Chiu und M. S. Rao, Humana Press, 2003). An overview of stem cell differentiation is provided by Robertson, Meth. Cell Biol. 75: 173, 1997 and Pedersen, Reprod. Fertil. Dev. 10: 31, 1998.

Methods relating to biological engineering techniques are described in "Bioprozesstechnik" (H. Chmiel Hrsg., Gustav Fischer Verlag 1991); "Bioreaktoren und periphere Einrichtungen. Ein Leitfaden für die Hochschulausbildung, für Hersteller und Anwender" (Winfried Storhas, Springer Verlag 1994); "Bioprocess Engineering Principles" (Pauline M. Doran, Academic Press 1997) and "Bioprocess Engineering: Basic Concepts" (Michael L-Shuler, Prentice Hall 2000). Reagents, media and kits described herein can be obtained from any known commercial provider, such as Sigma, Bio-Rad, Stratagene, and Roche.

The Median Specific Growth Rate:

The median specific growth rate for the cells is calculated according to the following differential equation, wherein $\mu$ is the specific growth rate, x is the number of cells and t is time: $dx/dt = \mu x$.

BRIEF DESCRIPTION OF THE FIGURES

FIG. 1: Growth curve of human embryonic stem cells (cell line H9.2) using different microcarriers. The cells were cultivated in a 20 ml volume in a spinner and agitated at 30 rpm with a glass ball agitator. Intermittent agitating phasing having an agitation time of 30 minutes and a resting time of 30 minutes was performed. The culture medium was conditioned by primary mice fibroblasts. Cytodex 3 (♦, Amersham) or CultispherG (■, Perbio) was used as the microcarrier source. The Y-axis represents the total cell number in the culture; the X-axis refers to the cultivation period represented in hours. The median specific growth rate ($\mu$) for cells on the Cytodex 3 microcarrier is $0.014\,h^{-1}$ compared to $0.013\,h^{-1}$ for control cells cultivated according to known techniques.

FIG. 3: Growth curve of human embryonic stem cells (cell line H9.2) on different microcarriers. The cells were cultivated in a 50 ml volume in a spinner and agitated at 20 rpm with a glass ball agitator. Intermittent agitation phasing having an agitation time of 30 minutes and a resting time of 30 minutes (♦) and continuous agitation (■), respectively, were performed. The culture medium was conditioned by primary mice fibroblasts. The Y-axis represents the total cell number in the culture; the X-axis refers to the cultivation period represented in hours. The median specific growth rate (μ) for the cells cultivated under continuous agitation is $-0.003\ h^{-1}$.

FIG. 4: Human embryonic stem cells (cell line H9.2) were cultivated on Cytodex3 microcarriers in a volume of 50 ml in a spinner. Agitation at 20 rpm using a glass ball agitator was performed. An intermittent agitation phasing having an agitation time of 30 minutes and a resting time of 30 minutes, or alternatively, continuous agitation, was performed. After 15 days of culturing in conditioned medium, a quantitative reverse transcription polymerase reaction (qRT-PCR) for detecting the pluripotency marker Oct4, Nanog, and Rex was performed. For calculating the relative gene expression, the ΔΔCP method was used, wherein the CP ("Crossing Point") value represents the number of PCR cycles that are necessary to achieve a constantly defined fluorescence level. At the CP, the same amount of newly synthesized DNA is present in all reaction tubes. The expression of the respective target gene is referred to as the expression of homogenously expressed reference gene, or a "housekeeping gene": ΔCP=CP target gene–CP reference gene. Following this standardization process, the ΔCP value of the control is subtracted from the ΔCP value of the samples as follows: ΔΔCP=ΔCP sample–ΔCP control. The relative difference in the expression (ratio) of a sample to the control, normalized to a reference gene, results from the formula ratio=$2^{-\Delta\Delta CP}$. If the relative difference of expression is below 1, the analyzed gene in the sample is down-regulated compared to the control; if the relative difference of express is greater than 1, the gene is up-regulated compared to the control. Glyceraldehyde-3-phosphate-dehydrogenase (GAPDH) was used as reference gene, while cells of line H9.2 served as control; the cells were cultured under conventional conditions in an adherent co-culture with mice fibroblasts. The Y-axis indicates the relative difference in expression of the pluripotency associated genes represented on the X-axis for embryonic stem cells cultivated under intermittent agitation (▤) or continuous agitation (▨).

FIG. 5: Human embryonic stem cells (cell line H9.2) were cultivated on Cytodex3 carriers in a spinner with glass ball agitator for 14 days. Intermittent agitation phasing at 20 rpm with an agitation time of 30 minutes and a resting time of 30 minutes was performed. To confirm that the embryonic stem cells cultivated in this manner remain pluripotent (i.e. are capable of forming by differentiation cells of all three germ layers), a spontaneous embryoid body formation of the embryonic stem cells in unconditioned serum containing medium was induced after 14 days of culturing. After three weeks, the embryoid bodies were fixed, slides were prepared and then stained using the germ layer-specific markers alpha-fetoprotein (endoderm), desmin (mesoderm), and cytokeratin (ectoderm). a: alpha-fetoprotein staining, b: nuclear staining (DAPI), c: overlay of the staining depicted in a and b; d: desmin staining, e: nuclear staining (DAPI), f: overlay of the staining depicted in d: and e:; g: cytokeratin staining, h: nuclear staining (DAPI), i: overlay of staining depicted in g: and h:.

DETAILED DESCRIPTION OF THE INVENTION

The present invention discloses a technical process enabling the cultivation and propagation of stem cells on a microcarrier in a bioreactor. Thus, for the first time, such a method is provided that is scalable, thereby allowing substantial augmentation of a cultivation volume. Following cultivation, the cells may be subjected to a variety of conditions that promote their differentiation into a wide variety of somatic cell types. The method of the disclosed invention also provides for the cultivation of large amounts of stem cells on an on-demand basis for the preparation of replacement tissue. This method is performed preferably in bioreactors, wherein it is possible to precisely regulate the desired culture conditions with respect to temperature, pH value, oxygen content and other experimental parameters. This precise regulation can be most efficiently achieved in a bioreactor, thereby allowing the cultivation of stem cells under strictly defined conditions, which are required to maintain the stem cell character of the cells as long as possible and to further prevent stem cell differentiation into somatic cell types.

Introduction of the Cells into the Container:

In one embodiment of the invention, the stem cells may be introduced into the container after the container has been established with medium and microcarriers. In a further embodiment, the stem cells are preincubated with the microcarriers suspended in medium. A precultivation is thus achieved, with the purpose of allowing the cells to optimally adhere to the microcarrier surface. This precultivation can be accomplished in the actual cultivation container or in a second container that is different from the container used for the cultivation. Moreover, this process can take place in any container suitable for the precultivation. During precultivation, the medium is not agitated or otherwise in motion. In particular, cell culture flasks are suitable for cultivating cells in suspension. Once the stem cells have adhered to, i.e. been loaded onto, the microcarriers, the microcarriers are then introduced into the container for the actual cultivation, i.e. the main cultivation, or if the precultivation was performed, in the same container as the main cultivation. At this stage, the medium is then subject to agitation within the container. Additional medium may be introduced into the container as appropriate.

Additionally, microcarriers that have not yet been loaded with the stem cells may be optionally introduced into the container. Once the loaded or unloaded microcarriers have been introduced into the container, the cultivation process commences. In a particularly preferred embodiment, the stem cells are embryonic stem cells. Particularly preferred are the use of stem cells that are embryonic germ cells, embryonic carcinoma cells, or the use of so-called embryonic stem cells (or "ES cells"), which can be isolated from the inner cell mass of a blastocyst. In a further embodiment, stem cells that have been derived from blood present in an umbilical cord, neuronal stem cells, mesenchymal stem cells derived from bone marrow, stem cells isolated and/or derived from the peripheral blood, the skin, pancreas, liver, gut, or from fat tissue are all suitable for use in the present invention. In a preferred embodiment, the stem cells are adult stem cells.

Removal of Cells from the Container

An advantage of the presently described method is the opportunity to remove the cells from the container at any desired point in time. This removal can be accomplished by sterile aspiration or by removing the medium containing the microcarriers. The removal of the cells may be performed for control purposes, to control the stem cell characteristics of the cells, or to effect an uninterrupted production of stem cells having a high quality and quantity for the subsequent differentiation to somatic cell types in the context of a continuous culture. This continuous control provides a safeguard that the characteristics of the stem cells are preserved. Such control is not available using known two-dimensional systems as the stem cells could possibly exhibit different characteristics depending on the individual culture dish. Furthermore, in two-dimensional systems, removing a portion of the cells is not typically an option or can only be achieved by substantially disturbing the remaining cells in the dish. By the use of a suspension culture, as provided by the method of the invention, cells may be readily removed from an already established culture, without the need to remove the culture as a whole. There is no known associated technical advantage in using a multiplicity of different culture dishes, typical of known two-dimensional cell culture methods, as each dish individually demands due care and control.

Upon removing the microcarriers with the adhered stem cells, new microcarriers may be introduced in order to allow a further expansion of the cells. The continuity of the culture is thus ensured, and the culture can be, for example, utilized for the differentiation of a large number of different cell types. Once the microcarriers comprising the stem cells have been removed, the cells can then be separated from the carriers via incubation with trypsin (for 5 minutes) or with collagenase (for 2 hours). This enzymatic treatment can be performed under agitation within a culture container. The subsequent separation of the cells from the carriers can be accomplished by sieving (following trypsin treatment) or by preplating the cells followed a rinse of the carriers (following collagenase treatment). It is also possible to plate the covered carriers onto cell culture dishes and to rinse off the remaining carriers once the cells have suitably grown onto the cell culture dishes.

In a further embodiment, the microcarriers covered with cells are not removed from the culture container; instead, the differentiation of the cells is initiated within the container.

Phase of Moving and then not Moving the Medium and the Cells

In one embodiment of the invention, a phase of non-movement, or "no agitation", occurs after the cells have been initially introduced into the carrier, thus allowing for the adhesion of the stem cells onto the microcarrier surface. In a preferred embodiment of the invention, the duration of the resting phase is maximally one day. In another preferred embodiment, the duration of the resting phase is maximally 12 hours. Once the adhesion of the cells is deemed complete, the medium can be moved or not moved in alternating phases. This particular phasing of movement provides the cells with a continuous steady exchange with the surrounding medium, thereby maximizing the use of the container volume and surface area. Moreover, the agitation ensures that the culturing conditions are uniform throughout the container. This feature is important for the uniform adjustment of all experimental parameters and provides yet another advantage over the two-dimensional culture, which must be carried out using a multiplicity of small, separated culture dishes that necessarily prevent uniform culturing conditions across the entire cell population.

However, agitating the medium possibly leads to the disadvantage that the resulting shearing forces impact the adhered cells, which may result in cells being dislodged from the surface and into the interior of the microcarrier. As a result, these cells are susceptible to death, thereby reducing the efficiency of the method with respect both to the total number of cells and maintaining the cells in an undifferentiated status. According to the invention, this problem is overcome by moving the medium in a manner whereby the shearing forces are minimized, specifically, by alternating a phase of agitating the medium with a phase maintaining the medium motionless. This phasing practice is herein referred to as "intermittent agitation". During the motionless resting phase, cells that have been dislodged into the microcarrier have an opportunity to re-adhere to microcarrier surface. This invention thus illustrates, in practice, that the intermittent agitation beneficially influences the survival rate of the stem cells, as well as their proliferation and their maintenance of stem cell characteristics.

In one embodiment of the present invention, the medium is agitated for a period of between 10 to 100 minutes and then remains motionless for a period of between 10 to 60 minutes, in an alternating fashion. In a preferred embodiment, the medium is agitated for a period of between 15 to 45 minutes alternated by a motionless period of between 15 to 45 minutes. In a particularly preferred embodiment, the medium is agitated for a period of between 20 to 35 minutes alternated by a motionless period of between 20 to 35 minutes. In the most preferred embodiment, the medium is agitated for 30 minutes alternated by a period of non-movement for 30 minutes. This intermittent agitation process can be carried out in a spinner bottle or in a regulated bioreactor having an agitator such as a glass ball, impeller or other suitable agitator. In one embodiment, the agitation can be performed at a velocity of between 20 and 200 rotations per minute (rpm). In a preferred embodiment, agitation is performed at a velocity of between 20 and 80 rpm. In the most preferred embodiment, the agitation is performed at 30 rpm.

Culture Medium

In one embodiment, the present inventive method is characterized in that the medium is conditioned before stem cells are introduced. "Conditioned" means that cells (i.e. non-stem cells) are cultivated within the medium to thereby modify the surrounding medium for optimal subsequent cultivation of the stem cells therein. Cells that are used to condition the medium are known as "feeder cells". The feeder cells are preferentially cultivated in the medium between 1 to 3 days, and in a more preferred embodiment, the feeder cells are cultivated for 1 day. Once the medium has been suitably conditioned by this precultivation with the feeder cells, the feeder cells are then separated from the medium prior to introducing the medium into a container for the subsequent cultivation of the stem cells. The separation of the feeder cells from the medium is preferentially performed using filters having a pore size smaller than the diameter of the feeder cells.

In a preferred embodiment, the feeder cells are mitotically inactivated prior to beginning the conditioning of the medium, preferably using gamma irradiation. The inactivation of the feeder cells thus prevents the propagation of these cells in the medium. Suitable cells for conditioning the medium include fibroblasts and/or other known cell types that can condition the medium for the optimal cultivation of stem cells. The fibroblasts can be of murine or human origin. The fibroblasts can further be genetically modified, for example, to express recombinant proteins that may be secreted into the medium. These recombinant proteins may be used for stimulating the proliferation of the stem cells and/or for preventing stem cell differentiation.

In a preferred embodiment, the ES cells are not removed from the cultivation container following the proliferation phase, wherein the stem cells have been propagated without losing the typical stem cell characteristics. Instead, a differentiation of these stem cells into somatic cells is initiated. In a particularly preferred embodiment, proteins are utilized for this purpose, said proteins capable of triggering the differentiation of the stems cells into a desired somatic cell type. Exemplary proteins include EGF (epidermal growth factor), PDGF (platelet-derived growth factor), retinoic acid, HGF (hepatocyte growth factor), and BMPs (bone morphogenetic proteins). These proteins may be secreted into the medium by genetically modified fibroblasts. In a preferred embodiment of the invention, the medium does not contain fetal calf serum. Instead, the cell cultivation can be achieved using a serum replacement substance. The medium can contain additional conditioning growth factors, such as bFGF, TGFβ1, LIF, flt3-ligand, and other factors that stimulate stem cell proliferation and/or prevent the cells from differentiating altogether.

Examples of suitable medium compositions include: Knockout-DMEM with 20% serum replacement, 1% non essential amino acids, 1 mM L-glutamine and 0.1 mM β-mercaptoethanol, 4 ng/ml bFGF, that was conditioned by murine fibroblasts for 24 hours, ExVivo (Cambrex) with 40 ng/ml bFGF and 15 ng/ml flt3-Ligand or Knockout-DMEM with 15% serum replacement, 1% non essential amino acids, 2 mM L-glutamine and 0.1 mM 2-mercaptoethanol, 4 ng/ml bFGF, 1000 U/ml LIF and 0.12 ng/ml TGFβ1.

Microcarriers

Microcarriers of the present invention are carrier materials, preferably spherical in form and suitable for cultivating adherent growing cells, in particular animal cells, in suspension. Microcarriers may be produced from a wide variety of materials, including plastic, glass, ceramic, silicone, gelatin, dextran, cellulose and others. In a particularly preferred embodiment of the invention, the microcarriers are produced from gelatin, dextran or cellulose. These materials may or may not be biologically degradable. The microcarriers may be composed of a uniform material or of a carrier material with a coating. The carrier material can be composed of gelatin, dextran, cellulose or another suitable material. The coating can include proteins or proteoglycans derived from the extracellular matrix of a mammalian cell. All proteins, modified derivatives of proteins or combinations thereof, are suitable for a coating which permits the adhesion of cellular material, in particular, proteins playing a biological role in cell-cell interactions including laminin, fibronectin, heparinsulfate, collagen, and matrigel. These derivatives can be produced via limited proteolysis, phosphorylation, glycosylation, genetic modification, alkylation, and other similar biophysiological methods. Gelatin is also suitable as a coating material. The microcarriers may also consist of known and commercially available materials including Cytodex 3, Cultispher G.

The coating of the carriers can be achieved by incubating the microcarrier in a solution of an appropriate protein under agitation. For example, the carrier material can be agitated in a 0.1% gelatin solution for a period of between 15 to 60 minutes or in matrigel (i.e. a solubilized basal membrane preparation obtainable from mice-derived EHS sarcoma; primary components include laminin, collagen IV, heparin-sulfate and entaktin; manufactured by Becton Dickinson) as diluted 1:10 in Knockout-DMEM for 2 hours. The solution is subsequently removed and the cells and medium are introduced. The density of the microcarriers may be between 0.9 and 1.1 g/ml. The median diameter $d_{50}$ of the carrier is between 125 and 300 μm. The carriers may be solid or porous, wherein the pore size may be between 10 and 30 μm.

Depending on the carrier type, between 1 g per 1 liter culture volume and 40 g per 1 liter culture volume are utilized in the present invention. If a non-regulated process is provided, the culture volume should not exceed 10 g carrier per 1 liter.

Scalability of the Method

An important aspect of the present invention is the opportunity to design a scalable process of cultivating stem cells. Therefore, a preferred embodiment is a method, wherein the container contains at least a 5 liter volume. In the most preferred embodiment, the container is characterized by a 100 liter volume. The method of the invention further provides for cell growth using an initial culture volume of less than 1 liter. Shortly before the cells have completely colonized the surface of the microcarrier, the culture volume is increased by the addition of fresh medium and/or microcarriers. Consequently, growth of the culture can be accomplished in a container larger than the size of the actual culture volume, so that new medium and/or new microcarriers may be added to the culture environment. In another embodiment, the volume of the container is equal to the culture volume, and an increase of the culture volume is achieved by transferring the culture volume into a new and larger container into which new medium and/or new microcarriers are provided. A preferred aspect of the invention is the ability to increase the culture volume by a factor of two. Particularly preferred is an embodiment of the invention, whereby the culture volume is increased by a factor of 10.

Periods of the Cultivation

The method of the present invention permits a continuous cultivation of the stem cells over an extended period of time, while preventing the cells from losing their typical stem cell characteristics. In one embodiment, this cultivation period is at least two weeks. In a more preferred embodiment, this cultivation period is at least four weeks. In an even more preferred embodiment, this period is at least six weeks.

Cultivation Conditions

The cultivation of the stem cells is performed at a suitable temperature, preferably at 37° C.

The invention is carried out at an oxygen concentration of between 1% and 25%, preferably at an oxygen concentration of 21%. In a further preferred embodiment, the oxygen concentration is between 3% and 6%. In a particularly preferred embodiment, the oxygen concentration is 4%. The above-described oxygen partial pressures values are herein disclosed at ranges (i.e. between 3% and 6%) that are not common in known cell culture techniques.

The cultivation is further performed at a $CO_2$-concentration in a range permitting the adjustment of the culture medium pH to a typical physiological value, preferably 5% $CO_2$.

Proliferation of the Stem Cells

The method of the present invention is particularly suitable for achieving a rapid proliferation rate of the cells in culture. One embodiment of the invention describes a method characterized in that the number of cells increases by at least 50% per week of cultivation, when compared to the number of cells present at the beginning of the week; such weekly increase being observable during the entire period of cultivation. A preferred embodiment of the invention is utilizing the presently described method to increase the number of cells by at least 75% per week of cultivation, or to a more preferred increase of 100%, or to an even more preferred increase of 150% when compared to the number of cells present at the beginning of the week; such weekly increase being observable during the entire period of cultivation. A particularly preferred embodiment of the invention is utilizing the presently described method to increase the number of cells by at least 200% per week of cultivation, when compared to the number of cells present at the beginning of the week; such weekly increase being observable during the entire period of cultivation. The present inventive method provides for a proliferation rate, wherein the number of cells is increased by 270% following six days of cultivation, compared to the number of cells present at the beginning of the week, as will be illustrated herein by way of example. Specifically, the number of cells is increased by over 300% over the course of one week. A preferred embodiment of the invention is thus use of the presently disclosed method to achieve an increase in the number of cells by at least 300% per week of cultivation, compared to the number of cells present at the beginning of the week; such weekly increase being observable during the entire period of cultivation and during the entire period of cultivation. Other preferred embodiments of the invention provide that the number of cells in the culture is increased by more than 300%. In the following examples, it is demonstrated that the number of cells is increased by 780% using the method of the present invention.

Therefore, a particularly preferred embodiment of the present inventive method is thus characterized in that the number of cells is increased by at least 400%, 500%, 600%, 700% or 800% per week of cultivation, when compared to the number of cells present at the beginning of the week; such weekly increase being observable during the entire period of cultivation.

One embodiment of the invention is utilizing the presently described method, wherein the cultivation is initially at a concentration below $10^6$ cells per milliliter. A preferred embodiment of the invention is use of the present method characterized in that the cultivation is initiated at a concentration below $10^5$ cells per milliliter. A particularly preferred embodiment of the invention is characterized by an initial cultivation concentration below $10^4$ cells per milliliter.

Maintaining the Stem Cell/Pluripotency Characteristics of the Introduced Stem Cells In one embodiment of the present invention, at least 70% of the cultured cells maintain their stem cell characteristics once the cultivation has been initiated. In a preferred embodiment of the invention, at least 80% of the cells maintain their stem cell characteristics once the cultivation has been initiated. In a particularly preferred embodiment of the invention at least 90% of the cells maintain their stem cell characteristics once the cultivation has been initiated. In an even more preferred embodiment of the invention, at least 95% of the cells maintain their stem cell characteristics once the cultivation has been initiated. By way of example, it is clearly illustrated that 97.7% of the cells express the known stem cell marker Oct4 following the start of cultivation. Thus, in a preferred embodiment of the invention at least 97% of the cells maintain their stem cell characteristics once the cultivation has been initiated. In a most preferred embodiment of the invention, at least 99% of the cells maintain their stem cell characteristics once the cultivation has been initiated. Both embryonic and adult stem cells are suitable for use in the present method. The use of either cell type yields a high proliferation rate, significant scalability of the process, and maintenance of the stem cell characteristics of the introduced cells.

Stem cell markers including Oct4 (described in Pesce M, Scholer H R. Oct4, Stem Cells 2001; 19:271-278), Tra-1-60 (described in Badcock, G., et al., 1999, Cancer Res. 59: 4715-4719.), Tra-1-81 (described in Henderson J. K. et. al. (2002), Stem Cells 20: 329-337), SSEA3, SSEA4 (described in Reubinoff B. E. et. al. (2000). Nature Biotechnology 18: 399-404), Nanog (Chambers I., et al., Cell. 2003 May 30; 113(5):643-55.) and other stem cell markers (the described stem cell markers herein are also discussed in: Brivanlou A H et al., Science. 2003 May 9; 300(5621):913-6 and Henderson J K et al., Stem Cells. 2002; 20(4):329-37) serve as suitable markers to detect the presence of stem cell characteristics in a cell population. The detection of such markers can be readily performed using antibodies directed to these stem cell markers followed by immunofluorescence labeling applied to the slides or via FACS analysis of the cells in solution. The number of stained cells detected herein shows the presence of stem cells. Further, a quantification of the expression of the detectable stem cell markers is possible using quantitative reverse transcriptase (RT) PCR, such as real-time-RT-PCR, competition-PCR or known techniques.

The percentage of cells having stem cell characteristics, which are subsequently introduced into the cell culture, should represent at least 80% of the cultivated cells. In one embodiment, this percentage is 95%. In a particularly preferred embodiment this percentage is 99%.

Containers

Containers useful for cultivating stem cells include containers that permit desirable movement of the medium, and further allow suitable control the experimental culture conditions. Such containers include roller bottles, spinner flasks, regulated bioreactors, and the like. Roller flasks are typically round cell culture bottles made of plastic or glass and having a culture area of between 400 and 2000 $cm^2$. The cells are readily cultivated along the entire inner surface of these flasks; the medium is applied to the culture via a "rolling" motion, i.e. rotating each bottle around its own axis.

Spinner flasks are typically glass containers (obtainable from e.g. Bellco Glass Inc. or Wheaton Scientific) having side arms for the purposes of supplying medium and also for inoculating the cells, and a magnetic agitator. Preferably, there is an elevated surface on the bottom of the flask that prevents the microcarriers from accumulating in the central portion of the flask.

A variation of a spinner is the known SuperSpinner. A SuperSpinner is a spinner that receives gas from a membrane agitator. The membrane agitator consists of a plastic support, encompassed by a microporous gassing membrane of polypropylene. The introduction of gas into the medium is performed in a gentle way so as to minimize any disturbance to the surrounding cells. Another suitable container includes an impeller agitator present in a spinner, i.e. a magnetic agitator to which a Teflon impeller is fixed.

Yet another suitable container includes a glass ball agitator in a spinner, consisting of a magnet embedded into a glass ball. A further variation of the agitator element includes a disk agitator. A disk agitator is a radially conveying agitator, while a propeller agitator generates an axial current. A paddle agitator and an INTERMIG agitator both convey axially, whereas an impeller agitator conveys in a direction that is tangentially to radially.

A regulated bioreactor is typically a glass or stainless steel container that is equipped with an agitator and a coating for maintaining temperature. At least one system for regulating oxygen partial pressure is present in the reactor. Preferably, the culture medium can be readily introduced and removed, thereby permitting a sampling so that, for example, the pH value can be adjusted.

In one preferred embodiment, the bioreactor has a gassing ring or a gassing basket to permit the introduction of gas into the medium. Another form of a bioreactor includes an air-lift fermenter. An air-lift fermenter is a bioreactor whereby the mixing is not performed mechanically; instead, the introduction of energy into the culture is achieved by the injection of compressed air from the bottom of the reactor. To allow an efficient circulation of the air, the system can operate using a conduit tube (i.e. a loop reactor).

One preferred embodiment includes a regular exchange of the culture medium. A particularly preferred embodiment is the daily exchange of the medium. The exchange of the culture medium can be performed continuously using an appropriate cell retaining system (as described below) or discontinuously by immediate exchange of the entire medium. The exchange of the medium can be readily performed under conditions that maintain sterility within the container. For containers that are small enough to be manipulated on a clean laboratory bench, the opening of the containers and the exchange of the medium can be performed on the clean bench. The old medium can thus be aspirated after the microcarriers have been sedimented, and then new medium can be easily introduced into the container. The transfer of microcarriers that are loaded with stem cells into a fresh container with fresh medium also represents a preferred embodiment of the invention. For containers that can not be properly handled on a clean laboratory bench, the use of cell retaining systems, or other like systems permitting a sterile exchange of medium are preferred.

In one embodiment, cell retaining systems guarantee continuity of the cell cultivation process. These systems allow an exchange of medium, if the cells including the carriers are to remain in the reactor. Preferred embodiments of cell retaining systems in connection with the method of the invention are spin filters and standpipes. The culture medium may be continuously removed using a spin filter in perfusion mode. The fluid phase is pressed into the interior of the spin filter by hydrostatic pressure. A sensor for the liquid level, introduced through the lid of the reactor, registers any decrease of the culture volume while fresh medium is pumped into the reactor. The cells are retained by the filter. With respect to a standpipe, the medium is aspirated from the top once the cells/carriers have been sedimented.

Such containers and systems and other related containers and systems suitable for the cultivation of cells in suspension are described in "Bioprozesstechnik" (H. Chmiel Hrsg., Gustav Fischer Verlag 1991).

Before any cultivation with the carriers is performed, the containers may be silanized using dimethyldichlorsilane in an organic solvent, which prevents adhesion of the cells onto the container surface. Once the silanization solution has dried, the containers are then rinsed with distilled water.

EXAMPLES

Example 1

$5.5 \times 10^5$ of human embryonic stem cells/per ml (cell line H9.2, Amit et al. (2000) Dev. Biol. 227: 271) are introduced together with 1.5 mg/ml Cytodex3 (Amersham) or 0.5 mg/ml CultisphereG (Perbio) microcarriers into a spinner (e.g. Bellco). Knockout DMEM with 20% serum replacement, 1% non essential amino acids, 0.5% L-glutamine and 0.1 mM 2-mercaptoethanol (Invitrogen) serve as the culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added. The culture volume is approximately 10 ml. Following an initial resting phase of one day, the medium volume is increased to 20 ml and an intermittent agitation phasing is initiated, achieved by using a glass ball agitator that is adjusted to impart a revolution speed of 30 rpm. Intermittent agitation having an agitation period of 30 minutes and a resting period of 30 minutes is applied. The oxygen partial pressure is about 21%. The pH value is maintained at a physiological value of between 7.2 and 7.4. The medium is completely exchanged on a daily basis.

Figure 1:
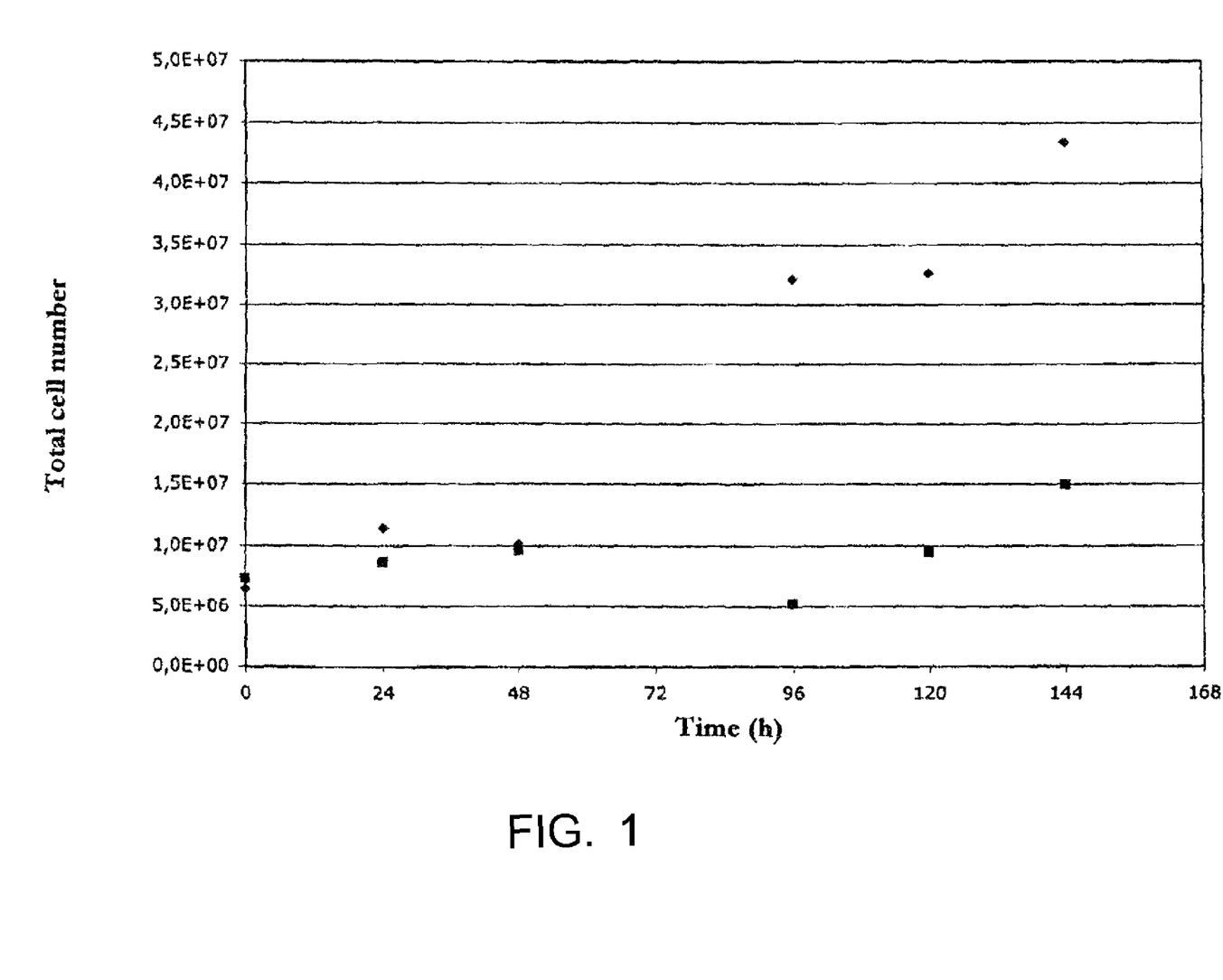
Figure 2:
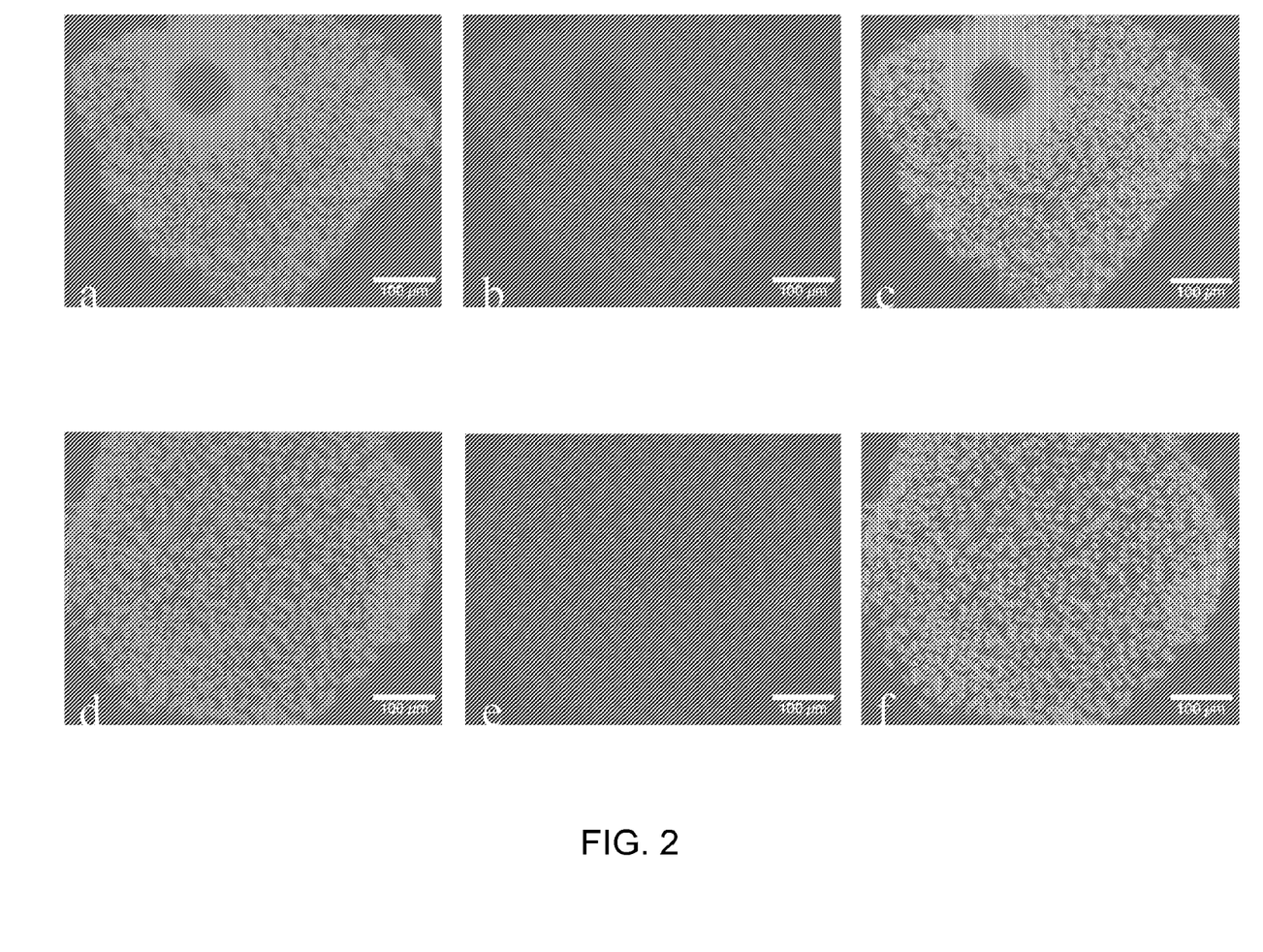
FIG. 2: Staining of human embryonic stem cells (cell line H9.2, Amit et al. (2000) Dev. Biol. 227:271) from a spinner (a: Oct4 staining, b: nuclear staining (DAPI), c: overlay of both staining methods) and a two dimensional cell culture (d: Oct4 staining, e: nuclear staining (DAPI), f: overlay of both staining methods) with pluripotency marker Oct4. The cells were cultivated for 240 hours in a spinner on Cytodex 3 carriers and agitated at 20 rpm with a glass ball agitator. The carriers were subsequently plated onto cell culture dishes and, after additional 72 hours, fixed and stained with the pluripotency marker Oct4. The control cells were cultivated using a two-dimensional system for 288 hours.

Following 10 days of culturing, the cells were removed, plated, and the microcarriers that had been incubated with Cytodex3 are then subjected to Oct4 staining. 97.9% of the cells present in the colonies, which were generated from the carrier cell aggregates after plating, are positive for the pluripotency marker (see FIG. 2). This result demonstrates the significant contribution of the inventive intermittent agitation feature on the successful maintenance of stem cell characteristics of the cultivated stem cells, thus providing a considerable advantage over known two-dimensional culture techniques. After six days of cultivation, the cell number markedly increased in comparison to the initial cell numbers, namely, by 780% and by 270% (Cytodex3 and CultisphereG, respectively) (see FIG. 1).

Example 2

$3.5 \times 10^5$ of human embryonic stem cells per ml (cell line H9.2) are introduced together with 1.5 mg/ml Cytodex3 (Amersham) or 0.5 mg/ml CultispherG (Perbio) microcarriers into a regulated bioreactor (e.g. Braun). Knockout DMEM with 20% serum replacement, 1% non essential amino acids, 0.5% L-glutamine and 0.1 mM 2-mercaptoethanol (Invitrogen) serve as the culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added. The culture volume is approximately 5 liters. Following an initial resting phase of one day, an intermittent agitation phasing is initiated. A revolution speed of 30 rpm is applied. The oxygen partial pressure is 5% in the reactor. The pH value is maintained at a physiological value of between 7.2 and 7.4. The medium is completely exchanged on a daily basis. Following cultivation for 10 days, the cells are removed from the container.

Example 3

$3.5 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner. Knockout DMEM with 20% serum replacement, 1% non essential amino acids, 0.5% L-glutamine and 0.1 mM 2-mercaptoethanol (Invitrogen) serve as culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added.

The culture volume is approximately 20 ml. Following an initial resting phase of one day, an intermittent agitation phasing is initiated. An impeller agitator is used, and a revolution speed of 20 rpm is applied. Intermittent agitation having an agitation period of 30 minutes and a resting period of 30 minutes is applied. The oxygen partial pressure is about 21% in the reactor. The pH value is maintained at a physiological value of between 7.2 and 7.4. The medium is completely exchanged on a daily basis. Following cultivation for 10 days, the cells are removed from the container.

Example 4

$3.5 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner. Knockout DMEM with 20% serum replacement, 1% non essential amino acids, 0.5% L-glutamine and 0.1 mM 2-mercaptoethanol (Invitrogen) are used as culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added.

The culture volume is approximately 20 ml. Following an initial resting phase of one day, an intermittent agitation phasing is initiated. A glass ball agitator is used to achieve a revolution speed of 20 rpm. The oxygen partial pressure in the reactor is about 21%. The pH value is maintained at a physiological value of between 7.2 and 7.4. The medium is completely exchanged on a daily basis. Following cultivation for 15 days, the cells are removed from the container.

Example 5

$3.5 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner. Knockout DMEM with 20% FCS (Hyclone), 1% non essential amino acids, 0.5% L-glutamine and 0.1 mM 2-mercaptoethanol and 4 ng/ml bFGF (Invitrogen) serve as culture medium.

The culture volume is approximately 20 ml. Following an initial resting phase of one day, an intermittent agitation phasing is initiated. An impeller agitator is used, to thereby achieve a revolution speed of 20 rpm. Intermittent agitation having an agitation period of 30 minutes followed by a resting period of 30 minutes is applied. The oxygen partial pressure in the reactor is about 21%. The pH value is maintained at a physiological value of between 7.2 and 7.4. The medium is completely exchanged on a daily basis. Following cultivation for 20 days the cells are removed from the container.

Example 6

$4 \times 10^5$ of human embryonic stem cells per ml (cell line H9.2) are introduced together with 1.5 mg/ml Cytodex3 (Amersham) or 0.5 mg/ml CultispherG (Perbio) microcarriers into a regulated bioreactor. Knockout DMEM with 15% serum replacement, 1% non essential amino acids, 0.5% L-glutamine, 0.1 mM 2-mercaptoethanol, and 4 ng/ml bFGF (Invitrogen), 1000 U/ml LIF (Chemicon) and 0.12 ng/ml TGFβ1 (R&D Systems) are used as culture medium.

The microcarriers are incubated together with the cells in a volume of 50 ml before introducing them into the container to allow for the adhesion of the cells. The microcarriers loaded with cells are subsequently introduced into a container having a culture volume of 500 ml. An impeller agitator is used; a revolution speed of 20 rpm is thus applied. An intermittent agitation phasing having an agitation period of 30 minutes followed by a resting period of 30 minutes is applied. The oxygen partial pressure in the reactor is about 21%. The pH value is maintained at a physiological value of between 7.2 and 7.4. The medium is completely exchanged on a daily basis. Every three days, the microcarriers are removed under sterile conditions in order to assess any observable stem cell characteristics. The removed medium is replaced by fresh medium. Following cultivation for 15 days, the cells are removed from the container.

Example 7

$3 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner. Ex Vivo (Cambrex) with 40 ng/ml bFGF (Invitrogen) and 15 ng/ml flt3-ligand (Preprotech) serve as the culture medium.

The culture volume is approximately 20 ml. Following an initial resting phase of twelve hours intermittent agitation is initiated. An impeller agitator is used, to thereby achieve a revolution speed of 20 rpm. Intermittent agitation phasing, whereby the agitation period is 30 minutes followed by a resting period of 30 minutes, is applied. The oxygen partial pressure in the reactor is about 21%. The pH value is maintained at a physiological value of between 7.2 and 7.4. The medium is completely exchanged on a daily basis. One-half of the medium volume containing the microcarriers is removed once per week, and replaced with fresh medium and fresh microcarriers. Following cultivation for 21 days, the cells are removed from the container.

Example 8

$3 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner. Knockout DMEM with 20% serum replacement, 1% non essential amino acids, 0.5% L-glutamine and 0.1 mM 2-mercaptoethanol (Invitrogen) serve as culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added.

The culture volume is approximately 20 ml. Following an initial resting phase of one day, intermittent agitation is initiated. A glass ball agitator is used, to thereby achieve a revolution speed of 30 rpm. Intermittent agitation phasing, with an agitation period of 30 minutes and a resting period of 30 minutes, is applied. The oxygen partial pressure in the reactor is about 21%. The pH value is maintained at a physiological value of between 7.2 and 7.4. The medium is completely exchanged on a daily basis.

After 14 days, the volume of the medium increased to 40 ml. The carrier concentration is maintained at 1.5 mg/ml for Cytodex3 (Amersham) or 0.5 mg/ml for CultispherG (Perbio) microcarriers. The medium is completely exchanged on a daily basis. Following a cultivation period of 4 weeks, the cells are removed from the container.

Example 9

$3.5 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner (e.g. B. Braun). Knockout DMEM with 20% serum replacement, 1% non essential amino acids, 0.5% L-glutamine and 0.1 mM 2-mercaptoethanol (Invitrogen) serve as culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added.

The culture volume is approximately 20 ml. Following an initial resting phase of twelve hours intermittent agitation is initiated. A glass ball agitator is used to achieve a revolution speed of 30 rpm. Intermittent agitation phasing having an agitation period of 30 minutes and a resting period of 30 minutes is applied. The oxygen partial pressure in the reactor is about 4%. The pH value is maintained at a physiological value of between 7.2 and 7.4. The medium is completely exchanged on a daily basis. Following cultivation for a total of 6 weeks, the cells are removed from the container.

Example 10

Constant Agitation $3.5 \times 10^1$ of human embryonic stem cells per ml (cell line H9.2) are introduced together with 1.5 mg/ml Cytodex3 (Amersham) or 0.5 mg/ml CultispherG (Perbio) microcarriers into a spinner (e.g., Bellco). Knockout DMEM with 20% serum replacement, 1% non essential amino acids, 0.5% L-glutamine and 0.1 mM 2-mercaptoethanol (Invitrogen) serve as culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added.

The culture volume is approximately 20 ml. Following an initial resting phase of 12 hours, agitation is initiated. A glass ball agitator is used, to thereby achieve a revolution speed of 20 rpm. The medium is completely exchanged on a daily basis. After cultivation for 15 days, the cells are removed from the container.

Example 11

Normoxic, Reactor $3.5 \times 10^5$ of human embryonic stem cells per ml (cell line H9.2) are introduced together with 1.5 mg/ml Cytodex3 (Amersham) or 0.5 mg/ml CultispherG (Perbio) microcarriers into a regulated bioreactor (e.g. B. Braun). Knockout DMEM with 20% serum replacement, 1% non essential amino acids, 0.5% L-glutamine and 0.1 mM 2-mercaptoethanol (Invitrogen) are used as culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added.

The culture volume is 5 liters. Following an initial resting phase of one day, agitation is initiated. A revolution speed of 30 rpm is applied. The oxygen partial pressure in the reactor is about 21%. The pH value is maintained at a physiological value of between 7.2 and 7.4. The medium is completely exchanged on a daily basis. Following cultivation for 10 days, the cells are removed from the container.

Example 12

Alternative Medium Composition $4 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner. Knockout DMEM with 20% serum replacement, 1% non essential amino acids, 0.5% L-glutamine and 0.1 mM 2-mercaptoethanol, and 40 ng/ml bFGF (Invitrogen), 0.5 µg/ml murine Noggin (R&D Systems) serve as culture medium. Following one day of static cultivation in a volume of 25 ml, the culturing volume is adjusted to 50 ml. An impeller agitator is used to thereby achieve a revolution speed of 30 rpm. Intermittent agitation phasing having an agitation period of 30 minutes followed by a resting period of 30 minutes is applied. The medium is completely exchanged on a daily basis. After cultivation for 10 days, the cells are removed from the container.

Example 13

$3.5 \times 10^5$ of human embryonic stem cells per ml (cell line H9.2) are introduced together with 1.5 mg/ml Cytodex3 (Amersham) or 0.5 mg/ml CultispherG (Perbio) microcarriers into a spinner (e.g. B. Braun). Knockout DMEM with 20% serum replacement, 1% non essential amino acids, 0.5% L-glutamine and 0.1 mM 2-mercaptoethanol (Invitrogen) are used as culture medium, which has been conditioned by gamma-irradiated primary mouse fibroblasts derived from mouse strain CD1 for 24 hours (for the preparation of fibroblasts: Siemen, H., Diplomarbeit 2003, Institut für Anatomie, Universität Regensburg). 140,000 fibroblasts per ml medium to be conditioned are used. Before application to the hESC culture, the conditioned medium is filtered and 4 ng/ml bFGF (Invitrogen) is added.

The culture volume is approximately 50 ml. Following an initial resting phase of twelve hours, intermittent agitation is initiated. A glass ball agitator is used to thereby reach a revolution speed of 20 rpm. Intermittent agitation phasing having an agitation period of 30 minutes and a resting period of 30 minutes is applied. The oxygen partial pressure in the reactor is about 21%. The pH value is maintained at a physiological value of between 7.2 and 7.4. The medium is completely exchanged on a daily basis. A parallel spinner culture served as a control, whereby continuous agitation instead of intermittent agitation phasing was utilized, while all other conditions remained unchanged.

Figure 3:
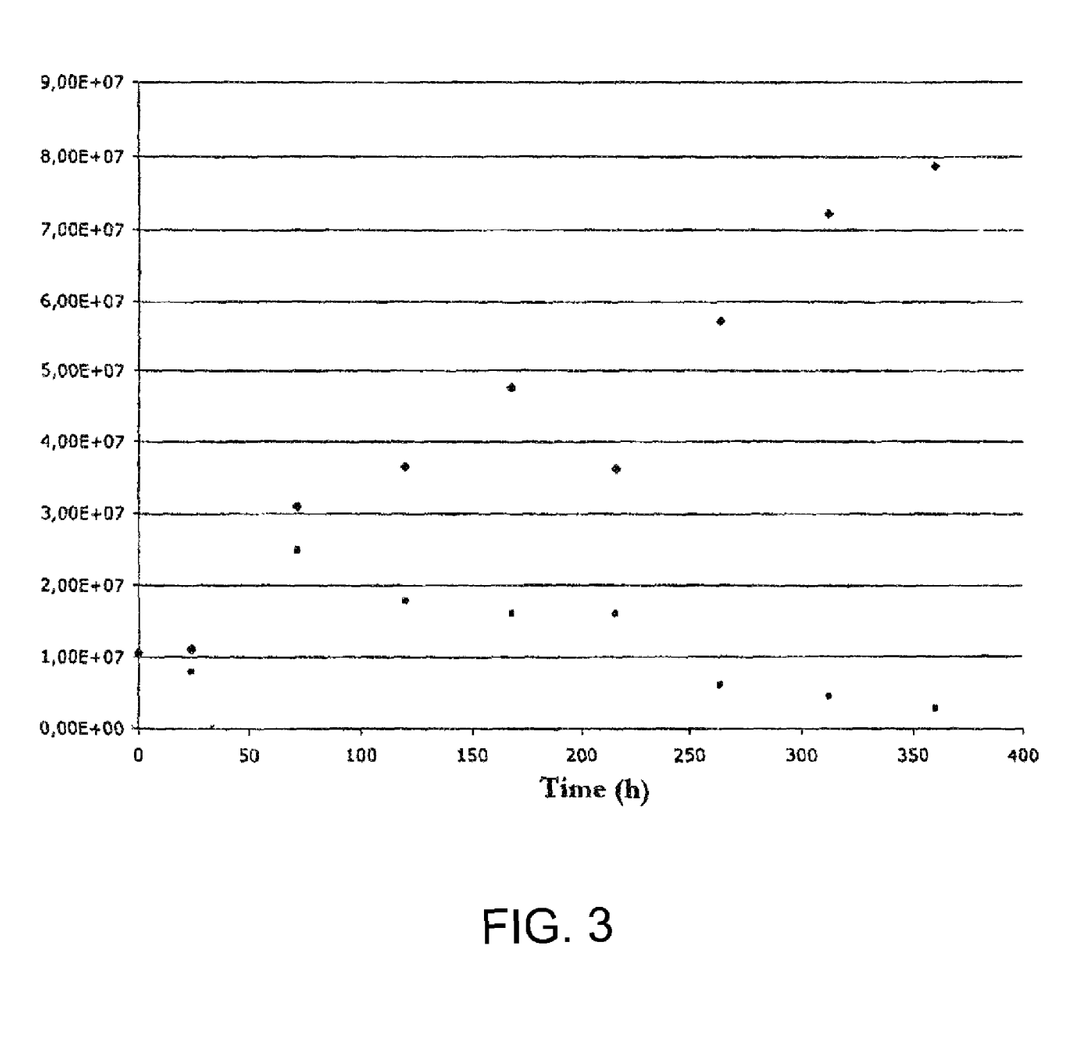

As illustrated by FIG. 3, the proliferation of stem cells that were cultivated using the inventive intermittent agitation feature of the invention is significantly higher when compared to the proliferation of cells cultured using a continuous agitation protocol. An increase of cell number is also observed under intermittent agitation conditions; a decrease of total cell number can be observed under the experimental conditions employing continuous agitation.

Example 14

The maintenance of pluripotent stem cell characteristics in the cultured cell population was measured under the same experimental conditions as described by Example 13, namely, using the intermittent agitation aspect and the continuous agitation as a control. Following 15 days of culturing in conditioned medium, a quantitative reverse transcription polymerase reaction was performed (qRT-PCR) in order to detect the pluripotency markers Oct4, Nanog, and Rex. For the purposes of calculating the relative gene expression, the known $\Delta\Delta CP$ method was used, wherein the CP ("Crossing Point") value represents the number of PCR cycles required to achieve a constant and defined fluorescence level. At the CP, the same amount of newly synthesized DNA is present in all reaction tubes. The expression of the respective target gene is referred to the expression of a homogenously expressed reference gene, or "housekeeping gene" and is defined by: $\Delta CP = CP$ target gene−CP reference gene. Following this standardization step, the $\Delta CP$ value of the control is subtracted from the $\Delta CP$ value of the samples by: $\Delta\Delta CP = \Delta CP$ sample−$\Delta CP$ control. The relative difference in expression (or ratio) of a sample to the control, normalized to a reference gene, is calculated by the formula ratio=$2^{-\Delta\Delta CP}$. If the relative difference of expression is below 1, the analyzed gene in the sample is considered to be down-regulated compared to the control gene; when this difference is above 1, the gene is deemed to be up-regulated compared to the control. Glyceraldehyde-3-phosphate-dehydrogenase (GAPDH) was used as reference gene and cells of cell line H9.2 served as the control; these control cells were cultured under conventional conditions in an adherent co-culture with mice fibroblasts.

Figure 4:
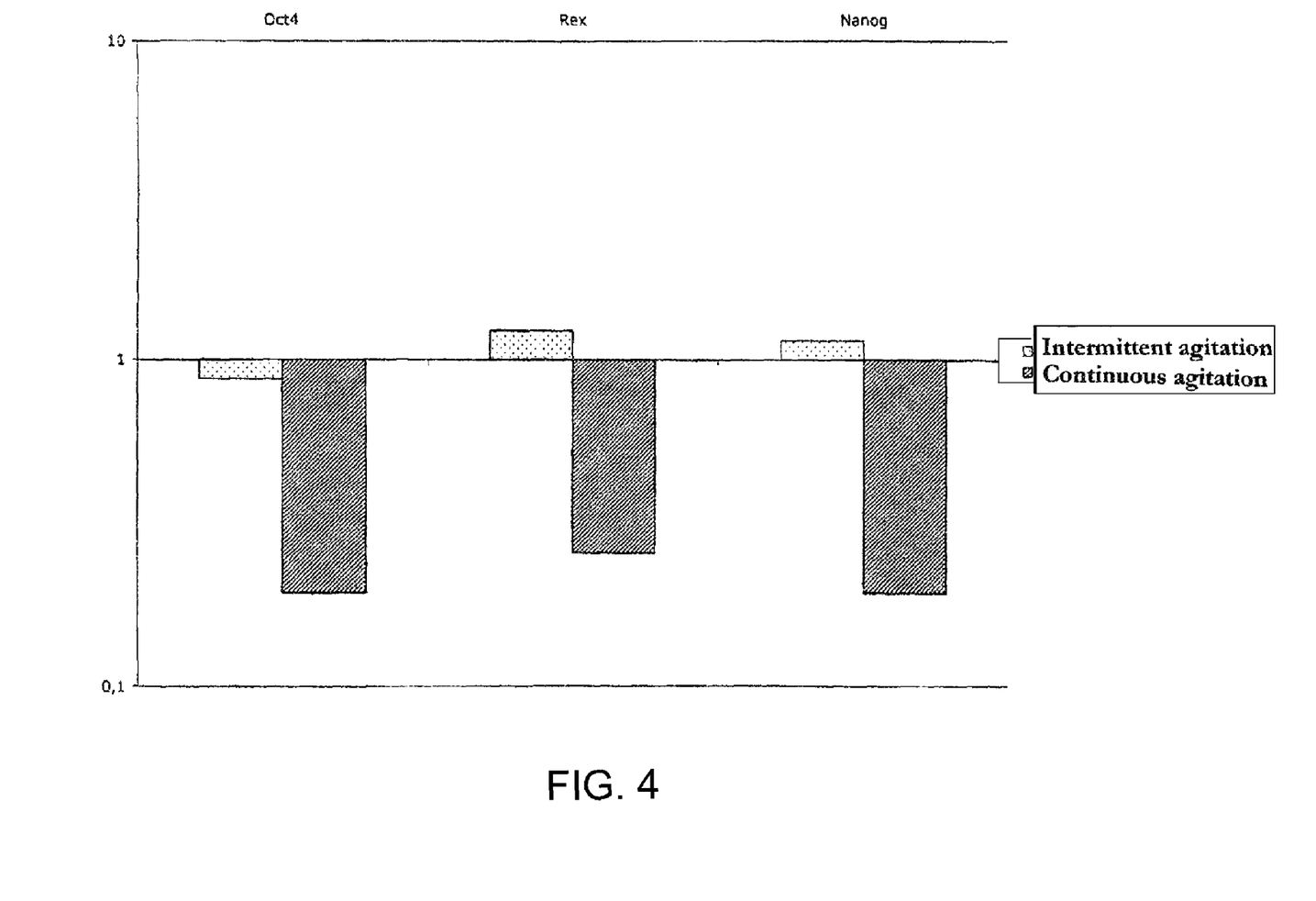

As is clearly shown in FIG. 4, the ES cells lose their cell markers for pluripotency/ES cell characteristics under experimental conditions of continuous agitation, thus indicating that ES cells wholly lose their pluripotency/ES cell characteristics. Moreover, FIG. 4 plainly illustrates that use of the intermittent agitation phasing feature of the present invention allows the maintenance of the pluripotency/ES cell characteristics. Therefore, the advantages of the presently described intermittent agitation technique in preserving stem cell characteristics and enhancing proliferation in culture when compared to continuous agitation protocols are thus clearly demonstrated.

Example 15

Cells cultivated with intermittent agitation are further capable of differentiating into cell types characteristic of all three germ layers. The stem cells were cultivated under the same culture conditions described by Example 14, i.e. utilizing intermittent agitation. To demonstrate that the embryonic stem cells cultivated in this manner maintain pluripotency, meaning these cells are capable of differentiating into cells typical of all three germ layers, a spontaneous embryoid body formation of the embryonic stem cells in non-conditioned serum containing medium was induced following 14 days of cultivation. After three weeks, the embryoid bodies were fixed, prepared on slides, and stained using the known germ layer-specific markers, alpha-fetoprotein (to detect the endoderm), desmin (mesoderm), and cytokeratin (ectoderm).

Figure 5:
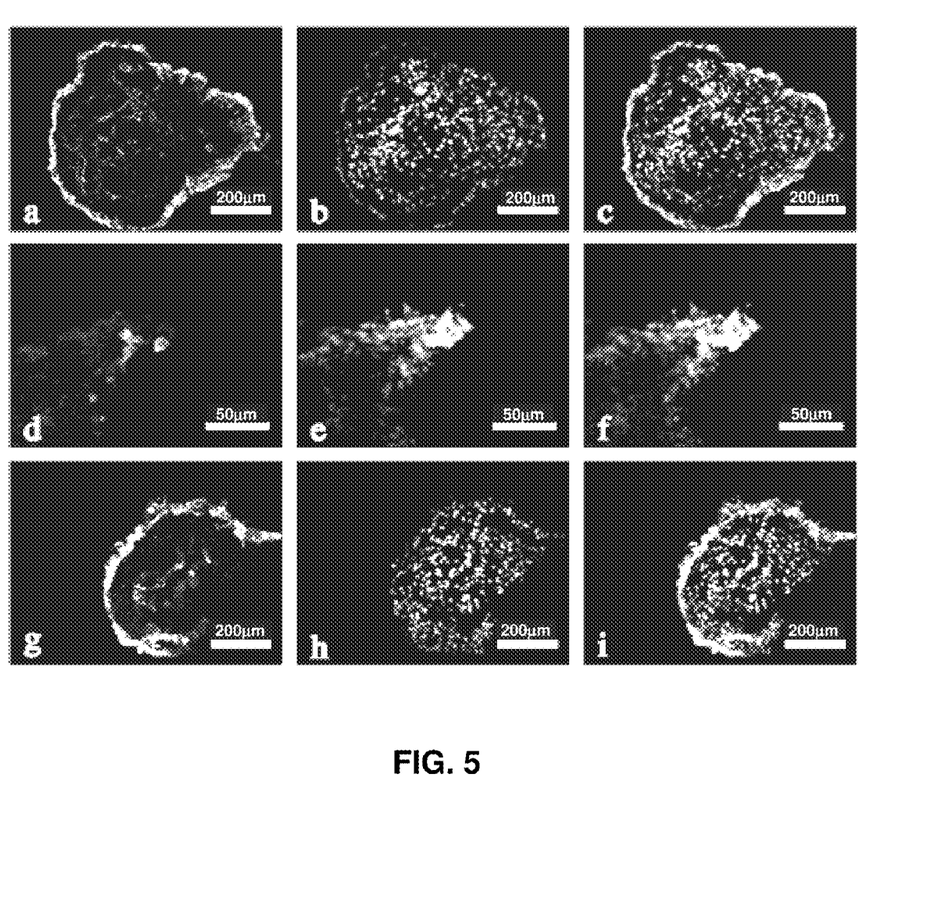

FIG. 5 clearly demonstrates that cells cultivated using the inventive intermittent agitation feature are capable of differentiating into the cell types typical of all three germ layers. Therefore, ES cells that have been cultivated using the described intermittent agitation phasing are not only capable of proliferating without losing their pluripotency and other ES cell characteristics, but are also capable of differentiating into the cell types comprising the three germ layers following specific stimulation.

We claim:

1. A method for proliferating stem cells, comprising: introducing medium, microcarriers and stem cells into a container, cultivating the stem cells on microcarriers in said container, wherein the cells do not lose their stem cell characteristics after having initiated the culturing, and removing the cells on the microcarriers from the container, wherein after having initiated the culturing the medium in the container is moved and not moved in an alternating manner, wherein the medium is moved between 10 and 100 minutes and is not moved between 10 and 60 minutes in an alternating manner.

2. The method according to claim 1, wherein the stem cells are incubated with the microcarriers before being introduced into the container to allow the stem cells to adhere to the microcarriers.

3. The method according to claim 1, wherein the stem cells are introduced into the container after medium and microcarrier have been introduced into the container.

4. The method according to claim 3, wherein following the introduction of the stem cells into the container a resting phase occurs, wherein during said resting phase the medium in the container is not moved for a maximum period of one day to allow the adhesion of the cells to the microcarriers.

5. The method according to claim 1, wherein the stem cells are embryonic stem cells.

6. The method according to claim 1, wherein the stem cells are adult stem cells.

7. The method according to claim 1, wherein the medium is moved between 15 and 45 minutes and is not moved between 15 and 45 minutes in an alternating manner.

8. The method according to claim 1, wherein said container is a spinner flask.

9. The method according to claim 8, wherein the moving in said container is effected by agitation with an agitator.

10. The method according to claim 9, wherein said agitation is performed at a speed of between 10 and 200 rpm of the agitator.

11. The method according to claim 1, wherein said container is a regulated bioreactor.

12. The method according to claim 1, wherein the medium is conditioned.

13. The method according to claim 12, wherein the medium is conditioned by cultivating the medium with non-stem cells for between 1 and 3 days.

14. The method according to claims 13, wherein the non-stem cells are removed from the medium before the stem cells are introduced.

15. The method according to claims 13, wherein the non-stem cells are fibroblasts.

16. The method according to claim 15, wherein the fibroblasts are genetically modified to express recombinant proteins and secrete said proteins into the culture medium.

17. The method according to claim 12, wherein the medium is conditioned by cultivating the medium with non-stem cells for one day.

18. The method according to claim 1, wherein the microcarriers consist of a carrier material and a coating.

19. The method according to claim 1, wherein the microcarriers consist of a uniform material.

20. The method according to claim 1, wherein the culturing continues for at least two weeks.

21. The method according to claim 1, wherein the culturing is performed at an oxygen partial pressure of between 1% and 25%, preferably at 21%.

22. The method according to claim 1, wherein the culturing is performed without fetal calf serum.

23. The method according to claim 1, wherein the culturing is performed with a serum substitute.

24. The method according to claim 1, wherein the culturing is performed in the presence of basic fibroblast growth factor (bFGF).

25. The method according to claim 1, wherein by the removal of cells from the container only a portion of the medium containing the microcarriers loaded with cells is removed and this portion of the medium is replaced by the introduction of fresh medium and new microcarriers not loaded with cells.

26. The method according to claim 1, wherein at least 90% of the cells maintain stem cell characteristics after the start of culturing.

27. The method according to claim 1, wherein at least 99% of the cells maintain stem cell characteristics after the start of culturing.

28. The method according to claim 1, wherein the number of cells increases by at least 50% per week of cultivation compared to the initial number of cells.

29. The method according to claim 1, wherein the number of cells increases by at least 600% per week of cultivation compared to the initial number of cells.

30. The method according to claim 1, wherein the cultivating of cells is initiated with a concentration of below $10^6$ cells per milliliter.

31. The method according to claim 1, wherein the cultivating of cells is initiated with a concentration of below $10^5$ cells per milliliter.

32. The method according to claim 1, wherein the cultivating of cells is initiated with a concentration of below $10^4$ cells per milliliter.

33. The method according to claim 1, wherein the cells are separated from the microcarriers after removing the cells with the microcarriers from the container.

34. The method according to claim 1, wherein the removing of cells is performed for assessing the maintenance of the stem cell characteristics.

* * * * *

UNITED STATES PATENT AND TRADEMARK OFFICE
CERTIFICATE OF CORRECTION

| | | |
|---|---|---|
| PATENT NO. | : 7,790,456 B2 | Page 1 of 1 |
| APPLICATION NO. | : 11/574804 | |
| DATED | : September 7, 2010 | |
| INVENTOR(S) | : Terstegge | |

It is certified that error appears in the above-identified patent and that said Letters Patent is hereby corrected as shown below:

On the Title page, item (22), the PCT Filing date should read:

--Sep. 7, 2005--

Signed and Sealed this
Eighth Day of March, 2011

David J. Kappos
*Director of the United States Patent and Trademark Office*